United States Patent
Dahlberg et al.

(10) Patent No.: US 10,240,117 B2
(45) Date of Patent: Mar. 26, 2019

(54) BIOREACTOR CONTAINER AND INTEGRITY CHECK METHOD FOR BIOREACTOR CONTAINERS

(71) Applicants: Martin Dahlberg, Bovenden (DE); Isabelle Gay, Peypin (FR); Lars Boettcher, Melsungen (DE); Stefan Obermann, Adelebsen (DE); Rainer Sandrock, Kassel (DE)

(72) Inventors: Martin Dahlberg, Bovenden (DE); Isabelle Gay, Peypin (FR); Lars Boettcher, Melsungen (DE); Stefan Obermann, Adelebsen (DE); Rainer Sandrock, Kassel (DE)

(73) Assignee: Sartorius Stedim Biotech GmbH (DE)

( * ) Notice: Subject to any disclaimer, the term of this patent is extended or adjusted under 35 U.S.C. 154(b) by 383 days.

(21) Appl. No.: 14/886,617

(22) Filed: Oct. 19, 2015

(65) Prior Publication Data
US 2016/0040109 A1    Feb. 11, 2016

Related U.S. Application Data

(62) Division of application No. 14/130,061, filed as application No. PCT/EP2012/002541 on Jun. 15, 2012, now Pat. No. 9,637,716.

(30) Foreign Application Priority Data

Jun. 30, 2011 (DE) .................. 10 2011 106 162

(51) Int. Cl.
C12M 1/34 (2006.01)
C12M 1/00 (2006.01)
(Continued)

(52) U.S. Cl.
CPC ............. *C12M 23/14* (2013.01); *A61J 1/10* (2013.01); *B32B 1/02* (2013.01); *B32B 3/30* (2013.01);
(Continued)

(58) Field of Classification Search
CPC ...... C12M 23/14; C12M 23/26; C12M 23/28; C12M 23/48; B65D 909/046; G01M 3/32;
(Continued)

(56) References Cited

U.S. PATENT DOCUMENTS 2,054,204 A    9/1936    McDonald
2,297,375 A    9/1942    Vogt
(Continued)

FOREIGN PATENT DOCUMENTS

DE    20 2012 005 987    8/2012
EP    0967472    12/1999
(Continued)

OTHER PUBLICATIONS

English language machine translation of JP-2000-109099 (dated Apr. 18, 2000), pp. 1-8. (Year: 2000).*
International Search Report dated Jan. 29, 2013.

*Primary Examiner* — William H. Beisner
(74) *Attorney, Agent, or Firm* — Gerald E. Hespos; Michael J. Porco; Matthew T. Hespos

(57) ABSTRACT

A bioreactor container comprising has an at least locally flexible wall and at least one container opening. The wall of the bioreactor container has a fluid-tight inner sheet, and an at least locally fluid-permeable or structured outer sheet. A method for testing the integrity of the bioreactor container also is provided.

5 Claims, 8 Drawing Sheets

(51) Int. Cl.
  *A61J 1/10* (2006.01)
  *B32B 1/02* (2006.01)
  *B32B 3/30* (2006.01)
  *B32B 5/02* (2006.01)
  *B32B 5/18* (2006.01)
  *G01M 3/22* (2006.01)
  *G01M 3/32* (2006.01)
  *G01M 3/04* (2006.01)
  *A61J 1/16* (2006.01)

(52) U.S. Cl.
  CPC .............. *B32B 5/022* (2013.01); *B32B 5/024* (2013.01); *B32B 5/18* (2013.01); *C12M 23/02* (2013.01); *C12M 23/26* (2013.01); *G01M 3/04* (2013.01); *G01M 3/22* (2013.01); *G01M 3/3218* (2013.01); *G01M 3/3272* (2013.01); *A61J 1/16* (2013.01); *B32B 2307/726* (2013.01); *B32B 2307/7265* (2013.01); *F04C 2270/0421* (2013.01)

(58) Field of Classification Search
  CPC .. G01M 3/329; G01M 3/3281; G01M 3/3218; A61J 1/10; B32B 1/02; B32B 3/30; B32B 5/022; B32B 5/024
  See application file for complete search history.

(56) References Cited

U.S. PATENT DOCUMENTS

| | | | |
|---|---|---|---|
| 3,813,923 A | | 6/1974 | Pendleton |
| 4,814,124 A | * | 3/1989 | Aoyama ................. B29C 55/02 |
| | | | 264/210.6 |
| 4,920,786 A | * | 5/1990 | Danielson ............ B65D 90/501 |
| | | | 220/560.03 |
| 5,988,422 A | | 11/1999 | Vallot |
| 9,534,980 B2 | * | 1/2017 | Dahlberg .............. G01M 3/329 |
| 2009/0022985 A1 | | 1/2009 | Smith et al. |

FOREIGN PATENT DOCUMENTS

| JP | 2000109099 A | * | 4/2000 |
|---|---|---|---|
| WO | 00/22398 | | 4/2000 |
| WO | 20081071358 | | 6/2008 |

* cited by examiner

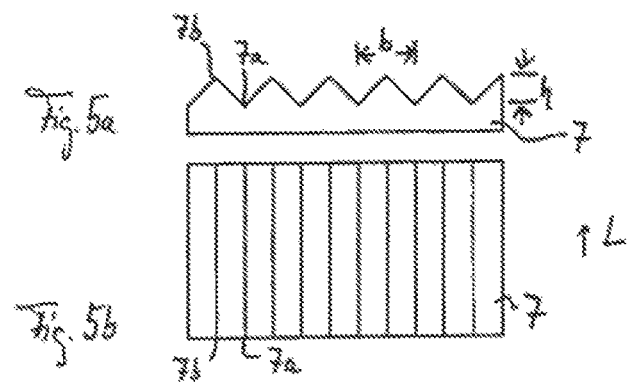
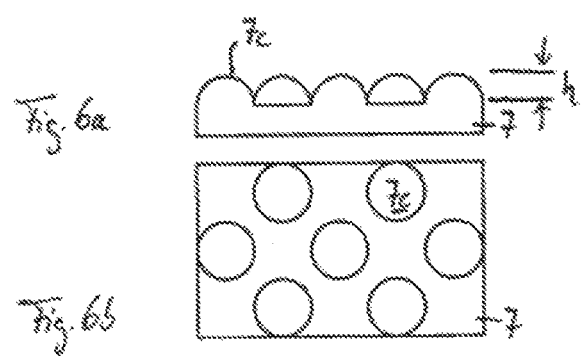
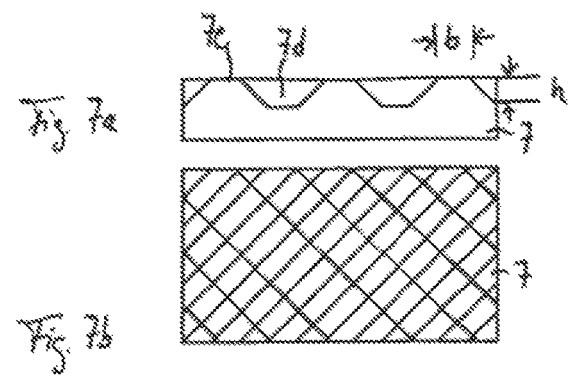

BIOREACTOR CONTAINER AND INTEGRITY CHECK METHOD FOR BIOREACTOR CONTAINERS

This application is a divisional of U.S. patent application Ser. No. 14/130,061 with a 371(c) date of Jan. 31, 2014, which is the US national phase of PCT/EP2012/002541, filed Jun. 15, 2012.

BACKGROUND

1. Field of the Invention

The present description relates to a bioreactor container and to a method for nondestructive testing of the integrity of bioreactor containers.

2. Description of the Related Art

In the pharmaceutical and biotechnology industries, flexible containers, for example bags, are used as bioreactor containers for processing or storage. The bioreactor containers may become damaged before actual use by the production process, transport or handling. It is therefore recommendable to carry out an integrity test of the bioreactor container before actual use. An integrity test is also expedient after use of the bioreactor container, in order to ascertain whether the integrity of the bioreactor container was maintained throughout the entire processing.

The term "bioreactor container" in the context of the application equally includes bioreactors and containers having locally flexible walls, which are used for example to receive, mix, store and dispense sterile media.

Conventional test methods for testing the integrity of the bioreactor container are the pressure drop method, flow measurement and trace gas analysis with the use of a test gas. A common feature of all the test methods is that a pressure difference is generated between the interior of the bioreactor container and a test apparatus containing the bioreactor container, or the surroundings of the bioreactor container. To this end, after production, or before and/or after use, the bioreactor container to be tested is arranged in a test apparatus for testing the integrity. This entails the risk that the bioreactor container to be tested will become damaged during the handling necessary for this, so that a leak is formed in the per se leaktight bioreactor container.

It is therefore an object of the invention to provide a bioreactor container and a method for testing the integrity of bioreactor containers, which allow improved integrity testing of the bioreactor container.

SUMMARY OF THE INVENTION

One aspect of the present invention relates to a bioreactor container comprising:
an at least locally flexible wall and
at least one container opening,
wherein the wall of the bioreactor container has at least one fluid-tight inner sheet, and wherein the wall of the bioreactor container has an at least locally fluid-permeable outer sheet.

Advantageously, the bioreactor container can be tested with respect to its integrity, or leaktightness, when the bioreactor container is located in a bioreactor container compartment of a bioreactor apparatus which is employed for intended use of the bioreactor container. Further handling of the bioreactor container, and therefore an additional risk of damage, are therefore advantageously avoided.

A bioreactor container comprises a fluid-tight wall, which is at least locally flexible. The term "bioreactor container" in the context of the invention equally includes bioreactors and containers having locally flexible walls, which are used for example to receive, mix, store and dispense sterile media. In particular, the bioreactor container has a wall which is formed from a film or a composite or laminate of a plurality of films. In other words, the bioreactor container may be formed as a bag. The bioreactor container is of variable volume. In other words, the internal volume of the bioreactor container can be increased by filling and decreased by emptying. For filling and emptying, the bioreactor container has at least one container opening. The at least one container opening is preferably formed as a gland or connector, so that fluid lines can be connected to the bioreactor container in a straightforward way by means of the at least one gland. During intended use, the bioreactor container is filled with starting substances or reactants through the at least one container opening, and the final substances or products are emptied through the at least one container opening. The filling and emptying of the bioreactor container preferably take place through two different container openings, so that the bioreactor container expediently has at least two container openings. It is to be understood that each of the at least one container openings is sealable, or is closed, fluid-tightly, in particular sterilely.

The leaktightness of the wall in relation to a fluid is ensured by a fluid-tight inner sheet of the wall. The inner sheet is in contact by one inner sheet side with the internal volume of the bioreactor container. In other words, during intended use the reactants or products of the biological, chemical or biochemical reaction, which is to be carried out or has been carried out in the bioreactor container, are in contact with the inner sheet. The inner sheet of the bioreactor container therefore preferably consists of a material which is biologically and chemically inert with respect to the reaction to be carried out, that is to say the inner sheet itself essentially does not react with the reactants or products in the biological or chemical sense. The inner sheet preferably consists of a polymer, for example polyethylene (PE) and/or polypropylene (PP). More preferably, at least the interior of the bioreactor container enclosed by the inner sheet is sterilizable, for example by means of steam, gassing with ethylene oxide, plasma treatment or gamma irradiation, so that the reaction can be started under sterile conditions. More preferably, the container openings are formed as sterile connectors or are fluidically connected to sterile connectors, for example through a tube. In the state ready for use, in particular at least the interior of the bioreactor container is sterile. More preferably, the entire bioreactor container is fully sterilized and sterilely packaged in the state ready for use. Preferably, the bioreactor container is intended for single use. In other words, the bioreactor container is a disposable product.

The inner sheet is at least locally, and preferably fully, flexible. It is to be understood that the inner sheet of the wall may be locally rigid. Particularly in the region of the one container opening, the inner sheet of the wall may be essentially rigid, so that the at least one container opening has a stable shape.

The wall of the bioreactor container comprises an at least locally fluid-permeable outer sheet. This means that the outer sheet is at least locally fluid-permeable, or the wall only locally comprises an outer sheet. In particular, the region of the wall which is flexibly formed has an outer sheet. Accordingly, for example, a rigid region of the wall may be formed merely as an inner sheet. As an alternative, the wall may be rigidly formed but have an outer sheet, which may not be fluid-permeable.

The outer sheet of the wall is fluid-permeable in the sense that a fluid which, contrary to intention, emerges from the interior of the bioreactor container through a leak of the inner sheet can also pass through the outer sheet. In other words, the outer sheet does not fulfill an additional sealing function. Rather, the function of the outer sheet is to separate the inner sheet from objects outside the bioreactor container so that such an object essentially does not come in direct mechanical contact with the inner sheet but merely comes in contact with the outer sheet, so that the mechanical stress on the inner sheet is also advantageously reduced. Furthermore, a leak in the inner sheet cannot be externally sealed by means of the object, since the outer sheet is fluid-permeable. A fluid emerging from the bioreactor container through the inner sheet would accordingly find a path through the fluid-permeable outer sheet to a position of the outer sheet which does not come in contact with the object, and can enter the surroundings there. Such an object may, for example, be a bioreactor container compartment of a bioreactor apparatus.

Bioreactor containers for carrying out a biological reaction may preferably have an internal volume of from about 5 milliliters to about 3000 liters, preferably about 2 liters, about 5 liters, about 10 liters, about 50 liters, about 100 liters, about 250 liters, about 500 liters or about 1000 liters. Usually, during intended use, bioreactor containers are filled with an aqueous solution so that the content of the bioreactor container has a mass of from about 5 g to about 3000 kg. Since the walls of the bioreactor container cannot in general withstand the internal pressure which is generated by the mass of the content of the bioreactor container, bioreactor containers are generally arranged in the bioreactor container compartment of the bioreactor apparatus, and fastened therein. In this case, the wall of the bioreactor container bears at least locally on the wall of the bioreactor container compartment, so that the bioreactor container compartment supports the wall of the bioreactor container. The walls of such bioreactor container compartments are usually formed from smooth stainless steel, in order to make contamination more difficult and to facilitate cleaning.

If an integrity test is then carried out after the bioreactor container has been arranged in the bioreactor container compartment, the interior of the bioreactor container being filled with a fluid in order to generate a positive pressure relative to the surroundings, the wall of the bioreactor container compartment could cover a possibly existing leak in the wall of the bioreactor container. Yet since the outer sheet of the wall of the bioreactor container is fluid-permeable, it is advantageously not possible for a smooth wall of the bioreactor container compartment to seal the leak in the wall of the bioreactor container by the wall of the bioreactor container being pressed against the wall of the bioreactor container compartment owing to the pressure prevailing inside the bioreactor container. This advantageously permits an improved integrity test, by which leaks in the wall of the bioreactor container can be determined with greater reliability, since it avoids a leak being inadvertently closed during the integrity test.

Furthermore, the integrity test of the bioreactor container can advantageously be carried out "in situ" before and/or after the experimental run, or the production process, that is to say when the bioreactor container is arranged in the bioreactor container compartment, which advantageously avoids additional handling of the bioreactor container and therefore a risk of damaging the bioreactor container by the additional handling.

The outer sheet is preferably porous, or comprises a porous material, the individual pore volumes expediently being connected to one another in such a way that the outer sheet is fluid-permeable. More preferably, the fluid-permeable outer sheet may have a direction-dependent, or anisotropic, fluid permeability. For example, the fluidic conductivity of the outer sheet in a direction parallel to the normal to the outer sheet surface may be greater than in a direction perpendicular to this normal, that is to say parallel to the extent of the outer sheet surface.

Preferably, the fluid-permeable outer sheet is connected releasably or nonreleasably to the fluid-impermeable inner sheet. The outer sheet may be connected fully or locally to the inner sheet, for example by adhesive bonding, welding or lamination. As an alternative, the outer sheet may also merely be drawn or pulled over the inner sheet. In other words, the outer sheet may be arranged releasably on the inner sheet or firmly connected to the inner sheet, or fastened on the inner sheet. The connection between the outer sheet and the inner sheet may also take place merely along connecting lines, connecting edges or at connecting corners. Accordingly, the outer sheet may be separated at least locally from the inner sheet, in which case the intermediate space between the outer sheet and the inner sheet may for example be filled with air or another gas.

Preferably, the fluid-permeable outer sheet comprises a woven textile, a nonwoven textile and/or a foam material. Nonwovens, for example spun nonwovens of polypropylene, may be used as preferred materials for the outer sheet. One such nonwoven is for example Novatexx 2019 Viledon from the company Freudenberg Filtration Technologies KG, made of polypropylene with a weight of 17-100 g/m2 and an air permeability of 1000-5000 l/m2 s at a pressure difference of 1 bar with a material thickness of 0.25-0.75 mm. Another exemplary material is available under the brand name Porex Porous Plastics XS XS49020-XS49100 from the company Porex Technologies GmbH. The material consists of polypropylene and polyethylene with a material thickness of from about 1.5 mm to about 5 mm, preferably more than about 3 mm. The size of the pores lies in the range of from about 20 µm to about 175 µm, preferably less than about 120 µm. The air permeability is from about 150 to about 300 l/cm2 min with a 1.2 inch water column. It has proven advantageous to use a polymer material which contains thermally conductive additives, for example boron nitrate, for the fluid-permeable outer sheet. In this way, temperature control of the bioreactor container can advantageously be improved.

Preferably, the inner sheet may comprise a plurality of inner sheet layers, which are connected to one another. For example, two or more inner sheet layers may be connected to one another by lamination. In this case, at least one of the inner sheet layers is fluid-tight. Preferably, all the inner sheet layers are formed fluid-tightly. At least one—preferably each—of the inner sheet layers is formed as a sterile barrier. In other words, microorganisms, bacteria, viruses, prions, etc. cannot penetrate the inner sheet, or the inner sheet layer(s), so long as the sterile barrier or barriers is/are intact.

In the context of the application, the term "flexible" includes both plastic and elastic deformability. The term "fluid" includes a gaseous phase, a liquid phase and also a mixture of liquid and gaseous phases of a substance.

One aspect of the present invention relates to a bioreactor container comprising:
an at least locally flexible wall and
at least one container opening, wherein the wall of the bioreactor container has a fluid-tight inner sheet, and wherein the wall of the bioreactor container has an at least locally structured outer sheet.

The bioreactor container corresponds in its properties essentially to the bioreactor container described above, the fluid-permeable outer sheet being replaced with a structured outer sheet, which may be fluid-permeable or fluid-impermeable. For this reason, the comments above relating to the bioreactor container, in particular relating to the wall, the container opening and the inner sheet, apply accordingly.

In the context of the application, a structured outer sheet means that at least the outer surface of the outer sheet is not smooth but has a structure, or a relief. In particular, the structure may be formed by elevations and depressions which are produced by variation of the material thickness of the outer sheet. That is to say, the outer sheet has a greater material thickness in the region of elevations than in the region of depressions. As an alternative, the material thickness of the outer sheet may be essentially constant, the structure being molded into the material. In this case, in particular, the flexibly formed region of the wall is provided with a structured outer sheet. Preferably, however, rigid regions of the wall may also have a structured outer sheet, or a structured outer surface. The outer surface refers to the face of the wall which lies away from, or opposite, the side of the wall facing the interior of the bioreactor container. Typically, the bioreactor container is gripped and handled on the outer surface.

In contrast to the alternatives described above, the outer sheet of the wall may be fluid-impermeable, so that the outer sheet can advantageously fulfill an additional sealing function. Nevertheless, the structured outer sheet leads to an equivalent technical effect as a fluid-permeable outer sheet, in the sense that a leak in the inner sheet cannot be externally sealed by means of an object. Owing to the structure of the outer sheet, an object cannot in general join fluid-tightly with the outer sheet in such a way that a fluid emerging from the bioreactor container through the inner sheet would not reach the surroundings. In particular, such sealing cannot take place by means of a bioreactor container compartment of a bioreactor apparatus. Accordingly, an integrity test can be carried out by applying a positive pressure to the bioreactor container, a pressure drop or a fluid flow due to the leak being detectable and making it possible to deduce that there is a leak.

As already described above, the bioreactor container may be arranged in order to carry out a biological reaction in the bioreactor container compartment of the bioreactor apparatus, the wall of the bioreactor container bearing at least locally on the essentially smooth wall of the bioreactor container compartment.

When an integrity test of the bioreactor container is carried out in the bioreactor container compartment, the structured outer sheet is pressed against the wall of the bioreactor container compartment. The effect of the structure of the outer sheet is that, owing to the arrangement of the outer sheet on the bioreactor container compartment, channels conveying fluid are formed between the two. In this way, a fluid penetrating the outer sheet through a leak can be delivered into the surroundings through the channels conveying fluid, so that the leak in the wall of the bioreactor container cannot be sealed by the wall of the bioreactor container compartment. As already described above, this advantageously permits an improved integrity test by which leaks in the wall of the bioreactor container can be determined with greater reliability, since it avoids a leak being inadvertently closed during the integrity test, and furthermore the integrity test of the bioreactor container can advantageously be carried out "in situ" before and/or after the experimental run, or the production process.

Preferably, the structured outer surface has depressions which are at least about 100 µm deep. In this case, two neighboring depressions define, or form, an elevation. Likewise, at least two neighboring elevations define, or form, a depression. More preferably, the depressions have at least a depth of more than about 150 µm, more preferably more than about 250 µm, and in particular more than about 500 µm, relative to the neighboring elevations. This ensures release of the fluid emerging from a leak into the surroundings.

Preferably, the structured outer side has elevations which are at most 200 µm wide. More preferably, the elevations have a width of less than about 150 µm, more preferably less than about 100 µm, and in particular less than about 50 µm. This prevents the possibility that an elevation can be positioned with an accurate fit on a leak and that the leak can thereby be sealed by a single elevation. The expected diameter of a leak is from about 5 µm to about 1000 µm.

Preferably, the elevations and/or depressions of the structured outer side are oriented along a preferential direction V. In particular, the elevations and/or depressions extend essentially along a longitudinal direction L, neighboring elevations and/or depressions being oriented parallel to one another. The preferential direction V in this case corresponds to the longitudinal direction L along which the elevations or depressions extend. In other words, the elevations and depressions may in particular form a groove structure or a rhombic structure on the outer sheet, or the outer surface.

Preferably, the structured outer sheet is connected releasably or nonreleasably to the fluid-impermeable inner sheet. The structured outer sheet may be connected fully or locally to the inner sheet, for example by adhesive bonding, welding or lamination. As an alternative, the structured outer sheet may also merely be drawn or pulled over the inner sheet. In other words, the structured outer sheet may be arranged releasably on the inner sheet or firmly connected to the inner sheet, or fastened on the inner sheet. The connection between the structured outer sheet and the inner sheet may also take place merely along connecting lines, connecting edges or at connecting corners. Accordingly, the structured outer sheet may be separated at least locally from the inner sheet, in which case the intermediate space between the structured outer sheet and the inner sheet may for example be filled with air or another gas. More preferably, the structured outer sheet is formed as a sterile barrier.

Preferably, the two alternative bioreactor containers described above are formed in such a way that the at least one container opening of the bioreactor container is enclosed in a first state by the outer sheet, the at least one container opening being freely accessible in a second state, and the bioreactor container being convertible from the first state to the second state by local removal of the outer sheet. In this case, the outer sheet may be fluid-permeable and/or structured.

Advantageously, the outer sheet may also be used as protection and/or sterile closure, or packaging, of the at least one container opening. In particular, in the first state the outer sheet may form a closed encapsulation around the other elements of the bioreactor container, which preferably packages these elements sterilely. During handling, the bioreactor container may be arranged in the bioreactor container compartment before subsequently being converted into the second state, for example by tearing the outer sheet, which can then preferably be pulled over a region of the bioreactor container compartment.

Preferably, the outer sheet may be formed from polyethylene, a composite or laminate of polyethylene and polypropylene, or a material which is known by the brand name Tyvek®. In particular, Tyvek® is permeable to steam so that sterilization of the bioreactor container can be carried out by means of steam, this material constituting a sterile barrier.

The invention also relates to a method for testing the integrity of a bioreactor container, having the steps:
providing a bioreactor container according to the invention;
providing a bioreactor apparatus having a bioreactor container compartment;
arranging the bioreactor container at least partially in the bioreactor container compartment;
connecting the at least one container opening of the bioreactor container to a fluid source;
filling the bioreactor container with a fluid from the fluid source in order to generate a predetermined positive pressure $P_1$ in the bioreactor container at a first time $T_1$, the outer sheet of the bioreactor container bearing at least locally on an inner wall of the bioreactor container compartment;
determining whether the bioreactor container is sufficiently leaktight.

In this case, the determination may in particular be carried out with the aid of a pressure difference (P2–P1) between a positive pressure P2 at a subsequent time T2 and the determined positive pressure at time T1. As an alternative or in addition, the determination may be carried out with the aid of a fluid quantity M which has been delivered to the bioreactor container after the time $T_1$, in order to keep the positive pressure $P_1$ constant. Furthermore, as an alternative or in addition, the determination may be carried out with the aid of detection, outside the bioreactor container, of fluid particles which have been delivered to the bioreactor container. Advantageously, the accuracy of the determination or ascertainment, and decision whether the bioreactor container is leaktight, can be increased when two or three of the quantities described above are detected. The probability that the leaktightness of the bioreactor container will be incorrectly classified or determined is thereby advantageously reduced.

An integrity test provides information about the integrity, or leaktightness, of the bioreactor container, in particular as to whether fluids can emerge from a leak or enter. In particular, the integrity is violated and the bioreactor container is unusable when microorganisms can enter the interior of the bioreactor container through a leak, so that the reaction inside the bioreactor container is compromised and the resulting products are unusable. Advantageously, the bioreactor container may bear on the inner wall of the bioreactor container compartment, the result of the integrity test not being influenced since sealing of existing leaks by the inner wall is avoided. In particular, an integrity test can be carried out when the bioreactor container is already contained in the bioreactor container compartment of the bioreactor apparatus with which the actual reaction is subsequently carried out.

The determination of whether the container is sufficiently leaktight may in particular be carried out by means of the pressure drop method, by measuring the fluid delivery rate at constant pressure, and by means of a test gas as the fluid. The test gas is expediently a gas which does not occur, or occurs only in traces, in the atmosphere, and can therefore be detected easily at the leak sites by means of a gas detector.

The positive pressure P1 of the fluid inside the bioreactor container relative to the atmospheric pressure is between about 20 mbar and about 500 mbar, preferably between about 50 mbar and about 300 mbar.

Preferably, the method comprises the subsequent steps:
filling the bioreactor container with reactants;
carrying out a chemical or biochemical reaction in the bioreactor container;
releasing the content from the bioreactor container.

Advantageously, the integrity test may be integrated into the production method, since the bioreactor container can be filled with the reactants, or starting substances of the reaction, directly following the integrity test. In order to remove the rest of the fluid used for the integrity test from the bioreactor container, the starting substances may expediently be delivered through a container opening located underneath on the bioreactor container, while the fluid is vented through a container opening located above, in particular through a sterile filter. Particularly in the case of starting substances containing protein, foaming is advantageously avoided.

Preferably, the determination of whether the bioreactor container is sufficiently leaktight is performed before and/or after the biochemical reaction is carried out in the bioreactor container. Preferably, the method comprises the steps following release:
connecting the at least one container opening of the bioreactor container to a fluid source;
filling the bioreactor container with a fluid from the fluid source in order to generate a predetermined positive pressure $P_1$ in the bioreactor container at a first time $T_1$, the outer sheet of the bioreactor container bearing at least locally on an inner wall of the bioreactor container compartment;
determining whether the container is sufficiently leaktight.

The determination is preferably carried out with the aid of a pressure difference (P2–P1) between a positive pressure P2 at a subsequent time T2 and the determined positive pressure at time T1. As an alternative, the determination is carried out with the aid of a fluid quantity M which has been delivered to the bioreactor container after the time $T_1$, in order to keep the positive pressure $P_1$ constant. Furthermore, as an alternative, the determination may be carried out with the aid of detection of fluid particles outside the bioreactor container, the fluid particles (for example a test gas) having been delivered to the bioreactor container.

In other words, after the end of the reaction a final integrity test may advantageously be carried out in order to check whether the bioreactor container has retained its integrity throughout the entire time of the reaction.

Preferred embodiments of the present invention will be explained by way of example below with the aid of the appended drawings. Individual features of the preferred embodiments presented may be combined to form other preferred embodiments.

BRIEF DESCRIPTION OF THE DRAWINGS

FIG. 5a shows a section through one embodiment of a structured outer sheet;

FIG. 5b shows a plan view of the structured outer sheet;

FIG. 6a shows a section through another embodiment of a structured outer sheet;

FIG. 6b shows a plan view of the structured outer sheet;

FIG. 7a shows a section through another embodiment of a structured outer sheet;

FIG. 7b shows a plan view of the structured outer sheet;

DETAILED DESCRIPTION OF THE PREFERRED EMBODIMENTS

Figure 1:
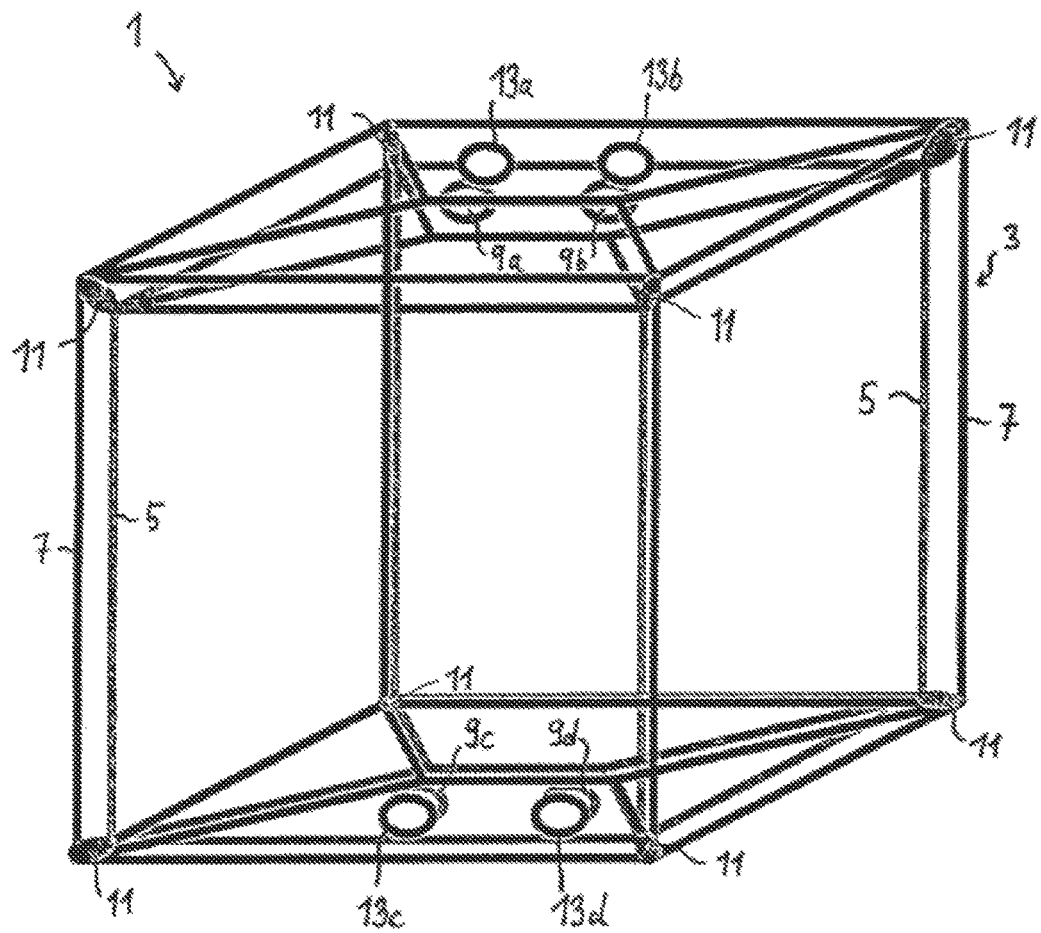
FIG. 1 shows a perspective view of one preferred embodiment of a bioreactor container.

FIG. 1 shows one preferred embodiment of a bioreactor container 1 in a perspective view. In this regard, it should be noted that the term "bioreactor container" in the context of the invention includes equally bioreactors and containers having locally flexible walls, which are used for example to receive, mix, store and dispense sterile media. The bioreactor container 1 comprises a wall 3 which has a fluid-impermeable, or fluid-tight, inner sheet 5 and a fluid-permeable outer sheet 7. The inner sheet 5 is formed from a nonporous flexible material, so that a variable internal volume is enclosed by the inner sheet. The internal volume of the bioreactor container 1 can be fluidically connected to the surroundings or to further elements, for example fluid lines, through the four container openings 9a, 9b, 9c, 9d. It is to be understood that the flexible inner sheet 5 may be formed more stiffly, or rigidly, in the region of the container openings, so that the container openings 9a, 9b, 9c, 9d have a stable shape and glands and connectors optionally connected thereto remain leaktight. The bioreactor container 1 can be filled and emptied through the container openings 9a, 9b, 9c, 9d. The outer sheet 7 is formed from a fluid-permeable porous material, which is arranged essentially separated from the inner sheet 5. The inner sheet 5 and the outer sheet 7 are in this case connected to one another pointwise in the region of the corners.

The bioreactor container 1 shown in FIG. 1 has a box-like or cuboid shape. The inner sheet 5 and the outer sheet 7 are therefore connected to one another at the eight corners of the box or cube. This connection may, for example, be carried out by welding or adhesive bonding, in particular on tabs 11 which protrude from the inner sheet 5 and/or the outer sheet 7. As an alternative or in addition, the inner sheet 5 and the outer sheet 7 may be connected, welded or adhesively bonded to one another in the region of the container openings 9a, 9b, 9c, 9d.

It is to be understood that the bioreactor container 1 may also have a tetrahedral, cylindrical, spherical, prismatic or other desired shape. The number of connecting regions at which the inner sheet 5 and the outer sheet 7 are then connected to one another can then be varied accordingly.

Irrespective of the external shape, the outer sheet 7 may be configured rigidly or flexibly. Advantageously, a rigid outer sheet 7 makes it possible that the bioreactor container always assumes a defined volume and that it can be handled by means of the rigid outer sheet 7 without exerting a pressure on the inner sheet during handling. As an alternative, the outer sheet 7 may be formed flexibly, so that the bioreactor container 1 can be easily folded and stored compactly. In the region of the container openings 9a, 9b, 9c, 9d, the outer sheet 7 preferably has access openings 13a, 13b, 13c, 13d through which the container openings 9a, 9b, 9c, 9d are accessible, or through which connectors or lines coming from the container openings 9a, 9b, 9c, 9d can protrude.

Figure 2:
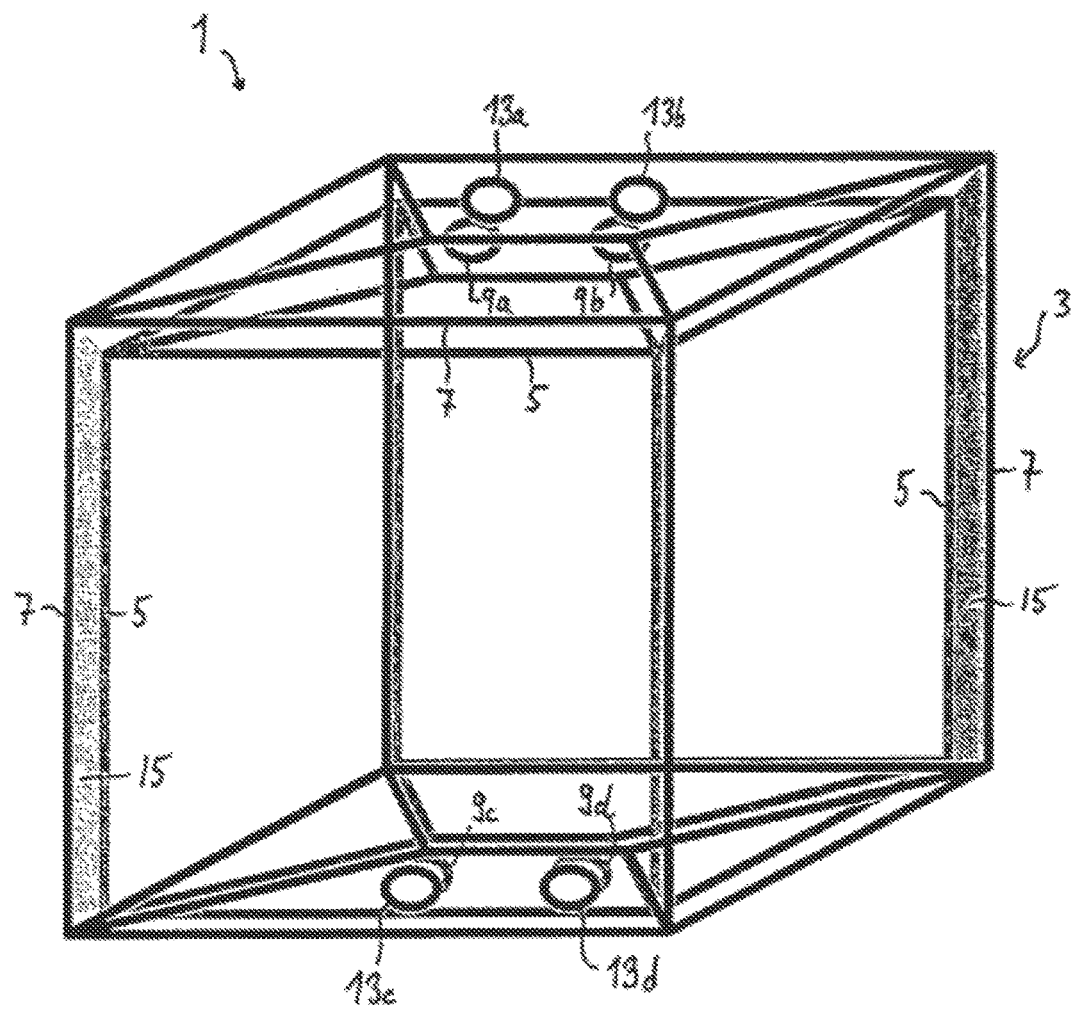
FIG. 2 shows a perspective view of another preferred embodiment of a bioreactor container.

FIG. 2 shows another preferred embodiment of a bioreactor container 1 in a perspective view. The structure of the bioreactor container 1 corresponds essentially to the structure of the bioreactor container 1 shown in FIG. 1, elements in FIG. 2 identical to FIG. 1 being denoted by the same references.

The bioreactor container 1 shown in FIG. 2 has an inner sheet 5 and an outer sheet 7, which are connected to one another along weld seams 13. Expediently, the inner sheet 5 and the outer sheet 7 are connected to one another on the edges of the wall 3, for example by welding or adhesive bonding. The linear connection of the inner sheet 5 to the outer sheet 7 advantageously leads to a more stable connection, which increases the torsional stiffness of the bioreactor container 1.

Figure 3:
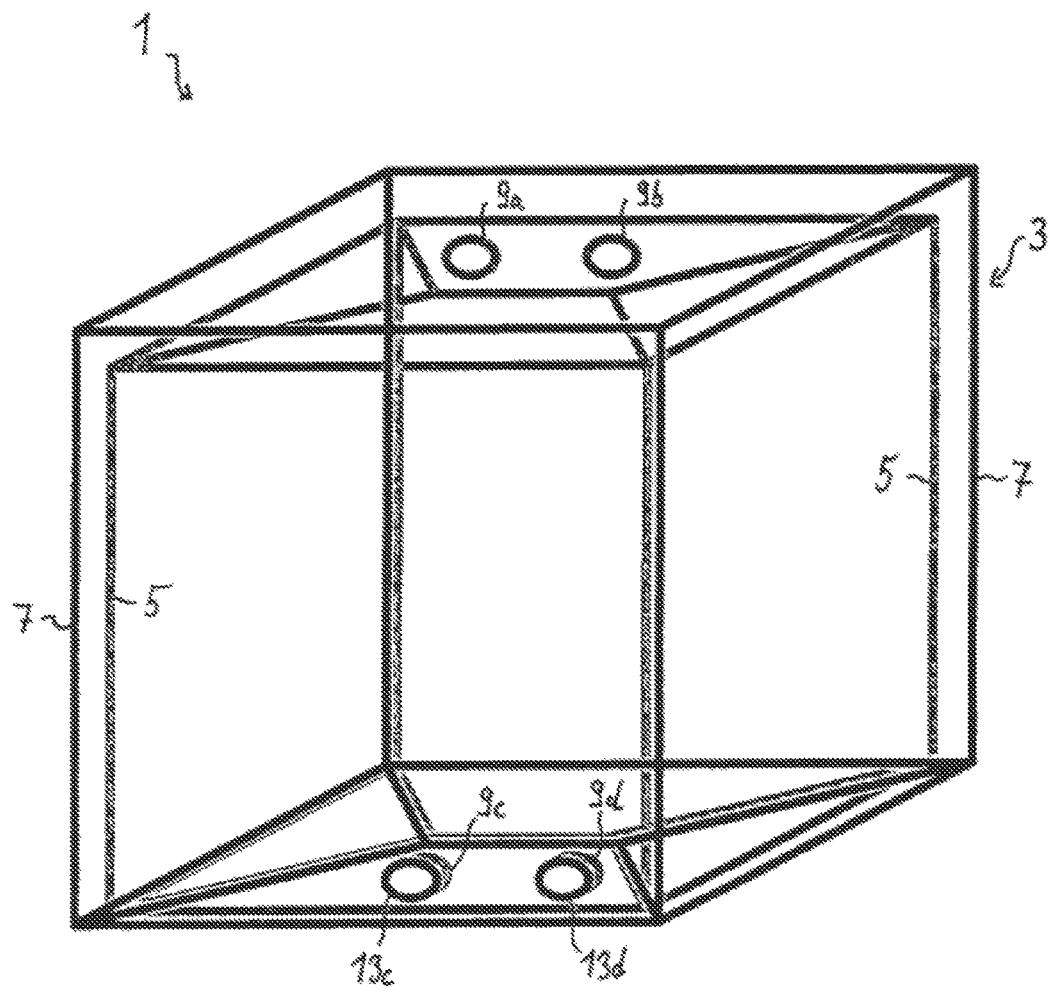
FIG. 3 shows a perspective view of another preferred embodiment of a bioreactor container.

FIG. 3 shows another preferred embodiment of a bioreactor container 1 in a perspective view. The structure of the bioreactor container 1 corresponds essentially to the structure of the bioreactor containers 1 shown in FIGS. 1 and 2, so that identical elements in FIG. 3 are denoted by the same references.

The bioreactor container 1 shown in FIG. 3 has an inner sheet 5 and an outer sheet 7, the outer sheet 7 only locally enclosing the inner sheet 5, or only locally being arranged on the inner sheet 5. In particular, the bioreactor container 1 does not have an outer sheet 7 on the side on which the container openings 9a, 9b are formed. This is not necessary in particular when the bioreactor container 1 does not come in mechanical contact with a bioreactor container compartment in this region during intended use. The inner sheet 5 and the outer sheet 7 may bear fully on one another, or be fully connected to one another. For example, the inner sheet 5 and the outer sheet 7 may be adhesively bonded or laminated to one another. It is to be understood that the outer sheet 7 may also merely be pulled releasably over the inner sheet 5. In particular, the outer sheet 7 may be delivered as one or more distinct elements separately from the rest of the bioreactor container 1, so that the outer sheet 7 is not arranged on the inner sheet 5 until intended use of the container. Expediently, the outer sheet 7 and the rest of the bioreactor container are delivered as a set inside a packaging unit.

Figure 4:
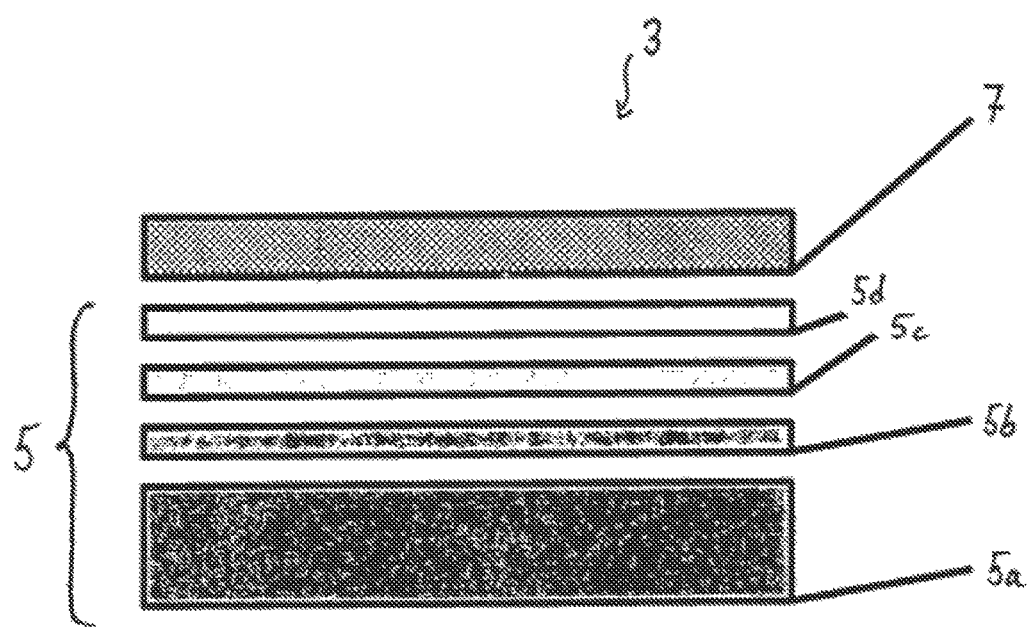
FIG. 4 shows a section through one embodiment of a wall having a fluid-tight inner sheet and a fluid-permeable outer sheet.

FIG. 4 shows a section through an embodiment of a wall 3 having a fluid-tight inner sheet 5 and a fluid-permeable outer sheet 7. In this preferred embodiment, the outer sheet consists of a porous layer of a nonwoven material or a foam material having continuous pores. Advantageously, the outer sheet 7 is mechanically durable and can therefore protect the underlying inner sheet 5 against mechanical influences.

In the preferred embodiment shown, the inner sheet 5 comprises a plurality of inner sheet layers 5a, 5b, 5c, 5d, which are connected to one another. For example, the inner sheet layers 5a, 5b, 5c, 5d may be connected to one another by lamination or adhesive bonding.

A contact inner sheet layer 5a consists of a material which is biologically or chemically inert with respect to the reactions to be carried out inside the bioreactor container, that is to say the inner sheet itself essentially does not react biologically or chemically. Preferably, the contact inner sheet layer 5a consists of a polymer, for example polyethylene (PE) and/or polypropylene (PP). In order to form the wall 3 fluid-tightly in the sense of gastightly, the inner sheet may have a gastight inner sheet layer 5b, or a gas barrier 5b. The mechanical stability of the wall may be produced by one or more mechanically supporting inner sheet layers 5c, 5d. These mechanically supporting inner sheet layers 5c, 5d may be formed fluid-tightly, but may also be fluid-permeable or gas-permeable if the contact inner sheet layer 5a and the gas barrier 5b ensure sufficient fluid-tightness.

As an alternative to the fluid-permeable or porous outer sheet 7, a structured outer sheet 7 may also be provided in the wall 3.

FIG. 5a shows a section through, and FIG. 5b shows a plan view of, one embodiment of a structured outer sheet 7. In this embodiment, the outer sheet 7 has depressions 7a and elevations 7b, which extend parallel to one another along a longitudinal direction L. In other words, the elevations 7b and depressions 7a form a groove structure on the outer sheet 7, or the outer surface. The elevations 7b and depressions 7a are formed by variation of the material thickness of the outer sheet 7. Preferably, the structured outer side comprises elevations which have a width b of at most about 200 µm, preferably about 50 µm, and a height h of at most about 200 µm, preferably about 50 µm.

FIG. 6a shows a section through, and FIG. 6b shows a plan view of, one embodiment of a structured outer sheet 7. In this embodiment, the outer sheet 7 has hemispherical elevations 7c, or pimples 7c. The pimples 7c are preferably arranged regularly on the outer sheet 7. The elevations or pimples 7c preferably have a height h of at most about 200 µm. The point bearing should be less than 5 µm, preferably less than 2.5 µm, but at any rate at most half the diameter of the hole size to be detected.

FIG. 7a shows a section through, and FIG. 7b shows a plan view of, one embodiment of a structured outer sheet 7. In this embodiment, the outer sheet 7 has depressions 7d and elevations 7e which form a rhombic structure on the outer sheet 7, or the outer surface. The elevations 7e and depressions 7d are formed by variation of the material thickness of the outer sheet 7, the elevations having a width b of at most about 5 µm, preferably about 2.5 µm, and a height h of at least about 100 µm.

It is to be understood that the elevations and depressions of the outer sheet 7 need not form a regular or periodic pattern, but may form an unordered, irregular structure.

Figure 8:
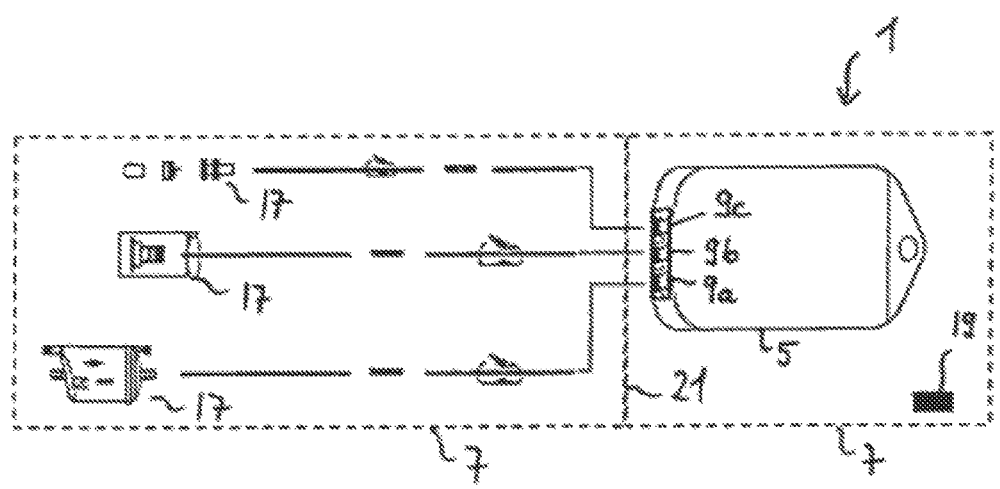
FIG. 8 shows a schematic view of one preferred embodiment of a bioreactor container.

FIG. 8 shows a schematic view of a preferred embodiment of a bioreactor container 1. FIG. 8 shows the bioreactor container 1 in a first state, the container openings 9a, 9b, 9c in the inner sheet 5 of the bioreactor container 1 being enclosed by the outer sheet 7. In other words, in the first state the outer sheet 7 forms outer packaging of the bioreactor container 1, which encloses, in particular sterilely encloses, the bioreactor container and in particular the container openings 9a, 9b, 9c and optionally components 17 connected to the container openings 9a, 9b, 9c, for example fluid glands, connectors, sterile connectors or sterile filters. Advantageously, the outer sheet 7 is thus used as protection and/or sterile closure or packaging of the bioreactor container 1, or its container openings 9a, 9b, 9c. The sterility state inside the outer sheet 7 of the bioreactor container 1, and optionally the sterility state of the components 17 enclosed by the outer sheet 7, may be documented by means of a sterility indicator 19. For example, the sterility indicator 19 may indicate, for example by coloration, whether the bioreactor container 1 has received a sufficient radiation dose during sterilization by means of gamma radiation.

For example by tearing the outer sheet 7 at a separation boundary 21, the bioreactor container can be converted into a second state, in which the container opening 9a, 9b, 9c, or the components 17 attached or connected thereto, are freely accessible. The outer sheet 7 may in this case be separated in such a way that the outer sheet 7 remains at least locally connected to the inner sheet 5. A part of the outer sheet either may be removed or is separated in such a way that this part can be folded or pulled back in order to obtain access to the container openings 9a, 9b, 9c, or the components 17 connected thereto.

Figure 9:
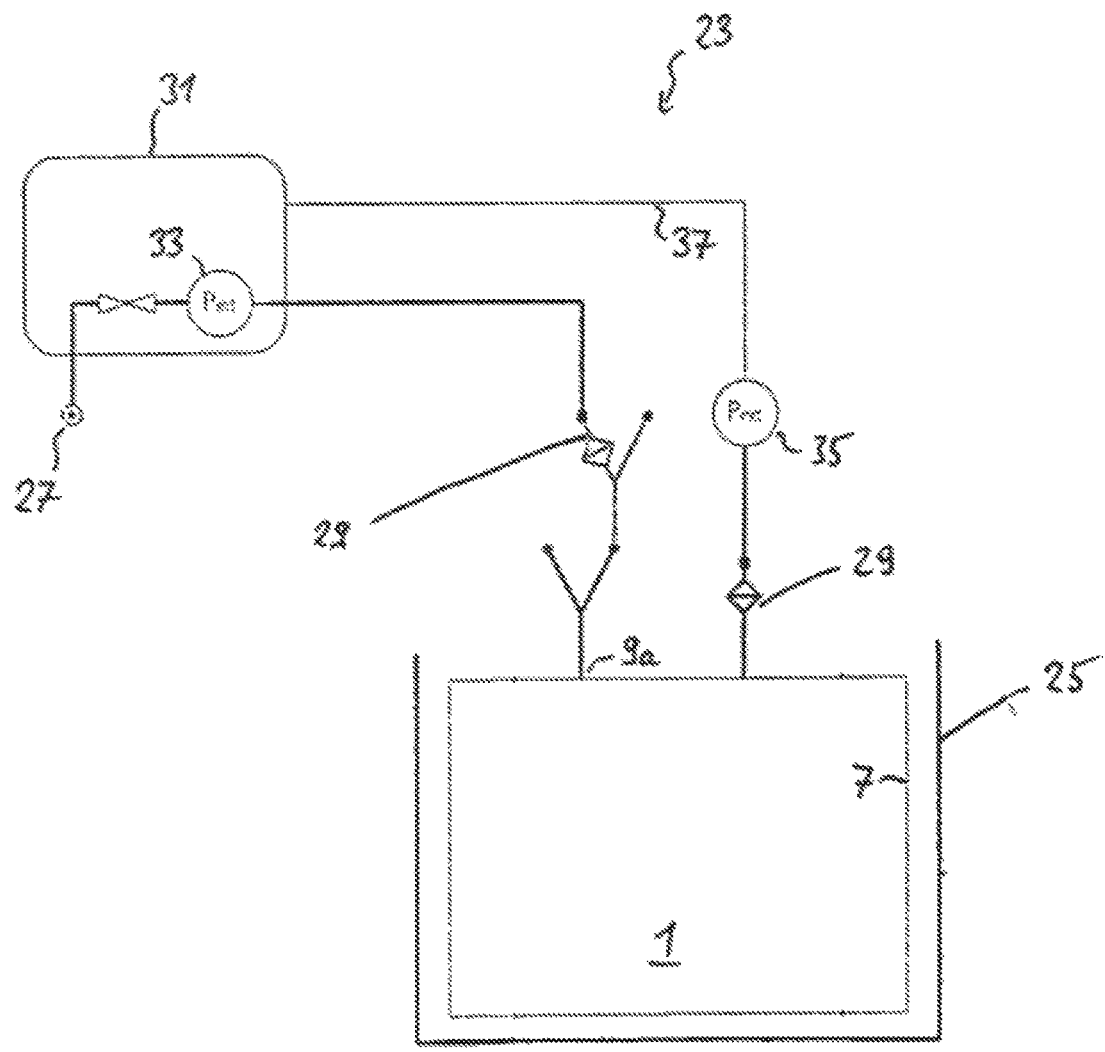
FIG. 9 shows a schematic view of an apparatus for testing the integrity of the bioreactor container.

FIG. 9 shows a schematic view of an arrangement 23 for testing the integrity of the bioreactor container 1. For the test, the bioreactor container 1 is arranged in a bioreactor container compartment 25 of a bioreactor apparatus. The at least one container opening 9a of the bioreactor container 1 is fluidically connected to a fluid source 27, for example by means of a sterile filter 29 in order to keep the interior of the bioreactor container 1 sterile. The fluid source may be part of a test apparatus 31, for example Sartocheck® 4plus from Sartorius Stedim Biotech GmbH, or it may be an external fluid source 27.

The bioreactor container 1 is filled with a fluid from the fluid source 27 at a time T1 with a predetermined positive pressure P1 of from about 50 mbar to about 100 mbar, the outer sheet 7 of the bioreactor container 1 bearing at least locally on an inner wall of the bioreactor container compartment 25.

The pressure difference P2–P1 between a positive pressure P2 at a subsequent time T2 and the determined positive pressure at time T1 may be detected by means of an internal pressure sensor 33 of the test apparatus 31. As an alternative or in addition, the pressure inside the bioreactor container 1 may be detected by means of an external pressure sensor 35. The external pressure sensor 35 is preferably connected to the test apparatus 31 via a signal line 37. With the aid of the pressure difference P2-P1, it is possible to determine whether the bioreactor container 1 is leaktight, or has integrity. To this end, the pressure difference must be less than a predetermined amount, in the ideal case equal to zero. Advantageously, the bioreactor container 1 may bear on the inner wall of the bioreactor container compartment 25 during the test, the result of the integrity test not being influenced since the sealing of leaks which exist by the inner wall is avoided owing to the configuration of the outer sheet 7.

Figure 10:
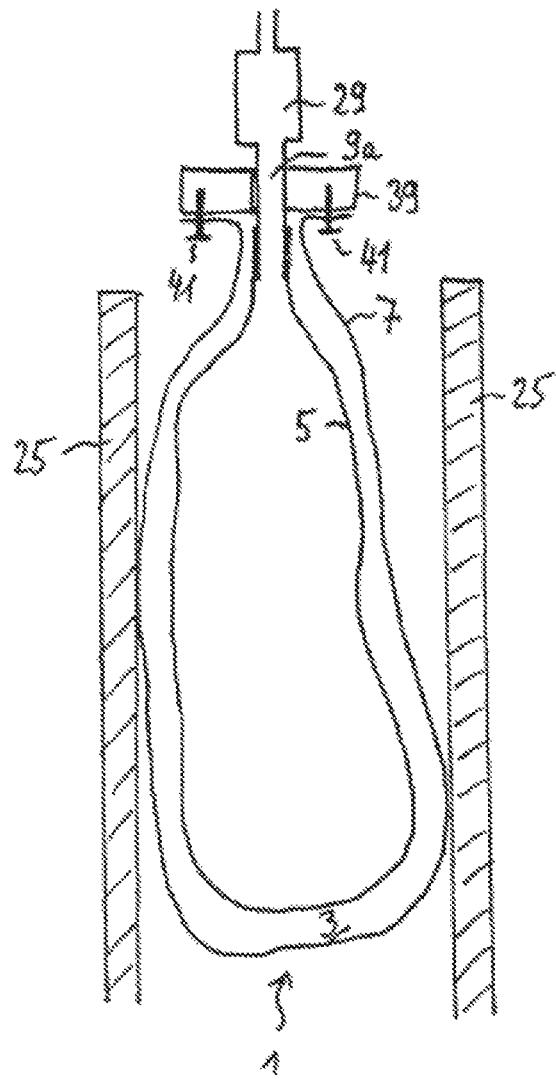
FIG. 10 shows one preferred embodiment of a bioreactor container.

FIG. 10 shows a preferred embodiment of a bioreactor container 1, which is arranged in a bioreactor compartment 25. The bioreactor container 1 comprises a wall 3, which has a fluid-impermeable inner sheet 5 and a fluid-permeable outer sheet 7. The wall 3 may preferably consist of a film, or a laminate of a plurality of films. In other words, the wall 3 may be formed essentially as a flexible bag, which can vary in shape. The inner sheet 5 is formed from a nonporous flexible material, so that a variable internal volume is enclosed by the inner sheet. The internal volume of the bioreactor container 1 can be connected fluidically to the surroundings or to further elements, for example fluid lines, by means of a container opening 9a and a sterile filter 29. The outer sheet 7 is formed from a fluid-permeable porous material or from a surface-structured material, which is arranged essentially separated from the inner sheet 5 and is connected releasably to the inner sheet 5 by means of a fastening device 39. To this end, the outer sheet 7 may be fixed on the fastening device 39 by means of fixing elements 41. After the test, the fixing elements, for example clamps or screws, may be released and the outer sheet 7 may be removed.

What is claimed is:

1. A bioreactor container (1) comprising:
   an at least locally flexible wall (3) that has a fluid-impermeable inner sheet (5) and an at least locally structured outer sheet (7), the structured outer sheet (7) being configured to separate the fluid-impermeable sheet (5) from an object outside the bioreactor container (1) so that the object from outside the bioreactor container (1) does not come in direct mechanical contact with the fluid-impermeable inner sheet (5) and so that a leak in the fluid-impermeable inner sheet (5) cannot be sealed by the object; and
   at least one container opening (9*a*, 9*b*, 9*c*, 9*d*) that is enclosed in a first state by the outer sheet (7), and that is freely accessible in a second state, wherein:
   the bioreactor container (1) can be converted from the first state to the second state by local tearing and removal of the outer sheet (7).

2. The bioreactor container (1) of claim 1, wherein the structured outer sheet (7) has depressions which are at least about 200 μm deep.

3. The bioreactor container (1) of claim 2, wherein the structured outer sheet (7) has elevations that are at most about 200 μm wide.

4. The bioreactor container (1) of claim 3, wherein the elevations and depressions of the structured outer sheet (7) are oriented along a preferential direction V.

5. The bioreactor container (1) of claim 1, wherein the structured outer sheet (7) is connected releasably or nonreleasably to the fluid-impermeable inner sheet (5), and
   wherein the outer sheet (7) is formed as a sterile barrier.

* * * * *